United States Patent [19]

Okawa

[11] Patent Number: 5,194,649

[45] Date of Patent: Mar. 16, 1993

[54] ORGANOPENTASILOXANE AND METHOD FOR ITS PREPARATION

[75] Inventor: Tadashi Okawa, Ichihara, Japan

[73] Assignee: Dow Corning Toray Silicone Co., Ltd., Tokyo, Japan

[21] Appl. No.: 825,906

[22] Filed: Jan. 27, 1992

[30] Foreign Application Priority Data

Jan. 29, 1991 [JP] Japan .................................. 3-27920

[51] Int. Cl.$^5$ ............................................... C07F 7/18
[52] U.S. Cl. ..................................... 556/451; 556/455
[58] Field of Search ............................... 556/451, 455

[56] References Cited

U.S. PATENT DOCUMENTS

| 3,881,536 | 5/1975 | Doran, Jr. et al. | 556/451 |
| 3,914,199 | 10/1975 | Lee et al. | 524/588 |
| 5,051,465 | 9/1991 | Yoshida et al. | 524/588 |

Primary Examiner—Marianne M. Cintins
Assistant Examiner—John Peabody
Attorney, Agent, or Firm—Edward C. Elliott

[57] ABSTRACT

This invention relates to an organopentasiloxane with the following formula

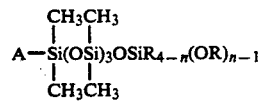

wherein A is the hydrogen atom or an aliphatically unsaturated monovalent hydrocarbon group, R is the same or different monovalent hydrocarbon group, and n is an integer with a value of 2 to 4, which carries silicon-bonded hydrogen or a silicon-bonded, aliphatically unsaturated monovalent hydrocarbon group at one molecular chain terminal and silicon-bonded organoxy group(s) at the other terminal.

3 Claims, No Drawings

ORGANOPENTASILOXANE AND METHOD FOR ITS PREPARATION

BACKGROUND OF THE INVENTION

1. Field of the Invention

The present invention relates to a novel organopentasiloxane and to a method for preparing same. More specifically, the present invention relates to an organopentasiloxane which carries at least 1 silicon-bonded organoxy group at one molecular chain terminal while silicon-bonded hydrogen or a silicon-bonded,-aliphatically unsaturated bond-containing monovalent hydrocarbon group (abbreviated below as aliphatically unsaturated monovalent hydrocarbon group) is present at the other molecular chain terminal. The present invention also relates to a method for the preparation of this organopentasiloxane.

2. Background Information

The triorganoxysilanes are already known within the class of organosilicon compounds which contain both Si-bonded hydrogen and Si-bonded organoxy groups, and this type of silane is used as a starting material for various types of silane coupling agent. In addition, vinyltriorganoxysilane and hexenyltriorganoxysilane, for example, are already known within the sphere of organosilicon compounds which contain both Si-bonded organoxy groups and the Si-bonded, aliphatically unsaturated monovalent hydrocarbon group, and these are used as starting materials for various types of silicone resins. These organoxysilanes are also useful as physical property improvers for composite materials made from one or more organic resins and one or more inorganic substances. These organoxysilanes possess 2 distinctly different types of functional groups, and, when interposed between organic resin and inorganic substance, they bond to both and function as a coupling agent. This serves to modify or improve the resulting physical properties.

However, when these organoxysilanes are employed, for example, as physical property improvers for silicone rubber, which after all is a type of composite material, the expected improvement is in fact not obtained.

The present inventor has engaged in continuous research over a number of years in order to solve the problem identified above. The present inventor has also been engaged in the constant study of methods for the synthesis of silanes and polysiloxanes containing the si-bonded organoxy group. It has been discovered as a result that a particular type of organopentasiloxane, which is distinct from the organoxysilanes already described above, is an effective physical property improver for silicone rubber. This organopentasiloxane is a novel, heretofore unknown compound. The present invention was achieved based on this discovery.

SUMMARY OF THE INVENTION the present invention relates to an organopentasiloxane with the formula

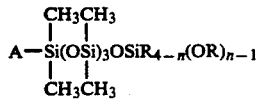

wherein A is the hydrogen atom or aliphatically unsaturated monovalent hydrocarbon group selected from the group consisting of the norborneyl group and alkenyl group, R is a monovalent hydrocarbon group wherein the groups R may be identical or may differ, and n is an integer with a value of 2 through 4. The organopentasiloxane is manufacturered by first reacting hemamethylcyclotrisiloxane and organohlaosilane with the formula

wherein A is the hydrogen atom or an aliphatically unsaturated monovalent hydrocarbon group and X is a halogen atom, in order to synthesize tetrasiloxane with the formula

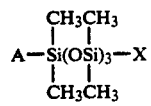

by then hydrolyzing said tetrasiloxane to afford alphahydroxytetrasiloxane with the formula

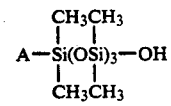

and by subsequently reacting said alpha-hydroxytetrasiloxane with organoxysilane with the formula

where R is a monovalent hydrocarbon group wherein the groups R may be identical or may differ, and n is an integer with a value of 2 through 4.

The present invention takes as its objects the above organopentasiloxane, a method for its preparation, and its use as a physical property improver for composite materials made from organic resin(s) and inorganic material(s).

DESCRIPTION OF THE INVENTION

This invention relates to organopentasiloxane with the formula

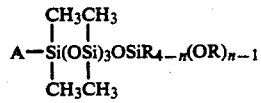

wherein A is the hydrogen atom or aliphatically unsaturated bond-containing monovalent hydrocarbon group, R is a monovalent hydrocarbon group wherein the groups R may be identical or may differ, and n is an integer with a value of 2 through 4.

This invention also relates to a method for the preparation of the above organopentasiloxane, wherein said method is characterized by reacting hexamethylcyclotrisiloxane and organohalosilane with the formula

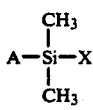

wherein A is the hydrogen atom or aliphatically unsaturated bond-containing monovalent hydrocarbon group and X is a halogen tom, in order to synthesize tetrasiloxane with the formula

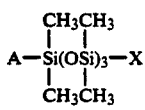

by then hydrolyzing said tetrasiloxane to afford alpha-hydroxytetrasiloxane with the formula

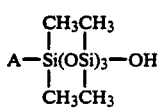

and by subsequently reacting said alpha-hydroxytetrasiloxane with organoxysilane with the formula

wherein R is a monovalent hydrocarbon group wherein the groups R may be identical or may differ, and n is an integer with a value of 2 through 4.

The organopentasiloxane according to the present invention has the following formula

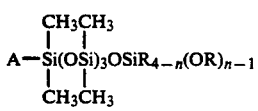

The group A in this formula is the hydrogen atom or an aliphatically unsaturated monovalent hydrocarbon group as exemplified by the norborneyl group and alkenyl groups such as vinyl, allyl, butenyl, hexenyl, isopropenyl, and so forth. The group A is preferably the hydrogen atom or vinyl group based on ease of synthesis and economics. When the group A is an aliphatically unsaturated monovalent hydrocarbon group, the corresponding organopentasiloxane as such may be employed as a coupling agent. However, when A is the hydrogen atom, the organopentasiloxane can also be employed as a starting material for coupling agents: its hydrosilylation reaction with any of various organofunctionalized unsaturated compounds afford the coupling agent. Said organofunctionalized unsaturated compounds are exemplified by allyl glycidyl ether, allyl methacrylate, and N-trimethylsilyallylamine. In the case of N-trimethylsilyallylamine, the product from the hydrisilylation reaction may be converted into the aminopropyl-functionalized coupling agent by removal of the trimethylsilyl protective group. R in the preceding formula encompasses monovalent hydrocarbon groups, and the groups R may all be identical or may differ. R is exemplified by alkyl groups such as methyl, ethyl, propyl, butyl, pentyl, and hexyl; by alkenyl groups such as vinyl, allyl, butenyl, hexenyl, and isopropenyl; by aryl groups such as phenyl, tolyl, and xylyl; by aralkyl groups such as benzyl and phenethyl; and by substituted alkyl groups such as chloroethyl and 3,3,3-trifuloropropyl. However, R is preferably methyl or ethyl based on ease of synthesis and economics, and methyl is particularly preferred. The subscript n in the preceding formula is an integer with values of 2 through 4: the coupling agent will be monofunctional for n=2, bifunctional for n=3, and trifunctional for n=4. In contrast to the prior silane coupling agents, in the organopentasiloxane according to the present invention a single silicon atom does not carry both the organofunctional and organoxy groups. By interposing highly flexible siloxane between the silicon atoms to which the organofunctional and organoxy groups are respectively bonded, the decline in the quantity of free organofunctional and organoxy groups which can participate in reactions is thereby avoided.

The preparative method according to the present invention proceeds first with the synthesis of tetrasiloxane with the formula

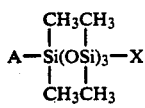

by the reaction of hexamethylcyclotrisiloxane with organohalosilane with the following formula

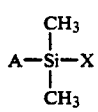

This reaction equation proceeds as follows.

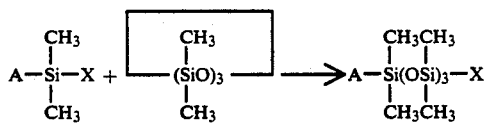

In the preceding formulas, A is the hydrogen atom or an aliphatically unsaturated monovalent hydrocarbon group, and A is exemplified by the hydrogen atom and by the aliphatically unsaturated monovalent hydrocarbon groups given as examples above. The group X is a halogen atom, e. g., fluorine, chlorine, bromine, or iodine. The group X is preferably chlorine based on ease of acquisition and economics. This reaction between organohalosilane and hexamethylcyclotrisiloxane according to the preceding reaction equation runs easily at room temperature in an aprotic polar solvent such as acetonitrile or dimethylformamide. Purification of the reaction mixture by distillation yields the target tetrasiloxane with the formula

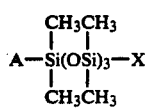

Hydrolysis of this tetrasiloxane product then affords alpha-hydroxytetrasiloxane with the following formula.

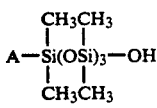

This reaction equation proceeds as follows:

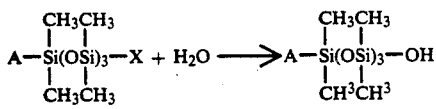

The tetrasiloxane hydrolysis according to the preceding reaction equation must be run very cautiously in order to prevent condensation of the Si-bonded hydroxyl groups produced by the hydrolysis. Thus, the recommended technique is to run this tetrasiloxane hydrolysis in dilute aqueous base solution while cooling.

The organopentasiloxane according to the present invention is finally prepared by reacting the aforesaid alpha-hydroxytetrsiloxane product with organoxysilane with the following formula:

This reaction equation proceeds as follows:

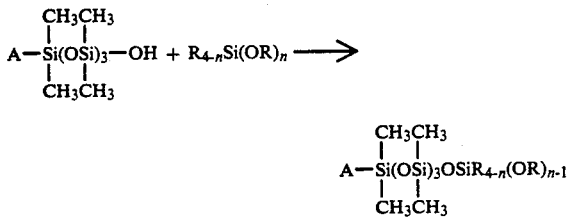

This condensation reaction between the alpha-hydroxytetrasiloxane and organoxysilane $R_{4-n}Si(OR)_n$ according to the preceding reaction equation is run by mixing the two reactants and heating. Preferred catalysts for this reaction are carboxylic acids such as acetic acid, propionic acid, and acrylic acid; inorganic acids such as carbonic acid, hydrochloric acid, and sulfuric acid; inorganic bases such as sodium hydroxide, potassium hydroxide, and lithium hydroxide; and amines such as triethylamine, pyridine, piperidine, quinoline, and diethylhydroxylamine. However, carboxylic acids are specifically preferred for their high catalytic activity, ease of post-reaction removal from the system by distillation, and absence of associated secondary reactions (e. g., chain scission reactions on the siloxane chain). Acetic acid and propionic acid are particularly preferred. The reaction temperature should fall within the range of 70° to 13° C. A satisfactory reaction rate is not obtained below 70° C., while exceeding 130° C. causes secondary reactions originating from siloxane chain scission.

In addition, in order to prevent condensation between the alpha-hydroxytetrasiloxane and the alcohol by-product from the condensation reaction and in order to shift the chemical equilibrium to the product side, the reaction is preferably run while removing the alcohol by-product from the system by thermal distillation. The alpha-hydroxytetrasiloxane organoxysilane $R_{4-n}Si(OR)_n$ molar ratio is not specifically restricted as long as the latter is present in excess. However, in order to prevent the dehydration reaction between the alpha-hydroxytetrasiloxane and alcohol by-product from the condensation reaction and in order to shift the chemical equilibrium to the product side, 3 to 10 times as much organoxysilane should be used on a molar basis as alpha-hydroxytetrasiloxne. The target organopentasiloxane according to the present invention can be recovered by purification of the reaction mixture by distillation.

The organopentasiloxane according to the present invention possesses silicon-bonded hydrogen or a silicon-bonded, aliphatically unsaturated monovalent hydrocarbon group at one molecular chain terminal and at least 1 silicon-bonded organoxy group at the other terminal. The organopentasiloxane according to the present invention can be employed as a coupling agent. For example, silicone rubber exhibits an excellent fatigue resistance when it contains reinforcing filler which has been treated with the vinyl-containing organopentasiloxane. When the Si-bonded hydrogen atom is present, various types of organofunctionalized organopentasiloxanes which evidence as improved reactivity can also by prepared, vide supra.

The following examples are included for illustrative purposes only and should not be construed as limiting the invention which is properly set forth in the appended claims. The number of cycles to failure represents the number of elongations until failure occurred.

EXAMPLE 1

First, 94.6 g (1 mole) dimethylchlorosilane, 222.5 g (1 mole) hexamethylcyclotrisiloxane, 6.8 g dimethylformamide, and 68 g acetonitrile were placed in a stirrer-equipped four-neck flask. After stirring for 1 hour at room temperature, distillation in vacuo afforded 186.9 g product. This was confirmed to be tetrasiloxane with the following structural formula by infrared absorption analysis (IR) and nuclear magnetic resonance analysis (NMR).

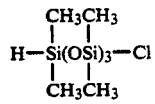

Next, 500 mL water, 500 g ice, 270 mL diethyl ether, and 39.7 g (473.3 mmole) sodium bicarbonate were placed in a stirrer-equipped four-neck flask and cooled to 0° C. A diethyl tetrasiloxane was then dripped in from an addition funnel while stirring. After the end of addition, the ether layer was removed in vacuo at room temperature to afford 97.5 g product. This was confirmed by IR and NMR to be tetrasiloxane with the following structural formula.

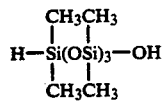

Next 80 g (267.9 mmole) of this tetrasiloxane, 122 g tetramethoxysilane, and 0.0304 mL propionic acid were placed in a four-neck flask equipped with stirrer and distillation set-up and were heated to 130° C. A mixture of tetramethoxysilane and methanol by-product was removed from the system by distillation, and fresh tetramethoxysilane was then added. The course of the reaction was monitored by gas chromatography (GLC): the process was repeated until the tetrasiloxane peak was extinguished. A total of approximately 300 g tetramethoxysilane was used. After termination of the reaction, the fraction at 83° to 89° C./1 mmHg was collected by distillation in vacuo to yield 79.8 g product. This was confirmed by IR and NMR to be pentasiloxane with the following structural formula.

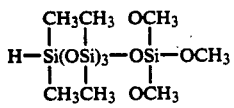

EXAMPLE 2

First, 216.5 grams (1.8 mole) dimethylvinylchlorosilane, 400 g (1.8 mole) hexamethylcyclotrisiloxane, 12.4 g dimethylforamide, and 123.4 g acetonitrile were placed in a stirrer-equipped four-neck flask. Stirring for 1 hour at room temperature followed by distillation in vacuo afforded 222 g of product. This was confirmed by IR and NMR to be tetrasiloxane with the following structural formula:

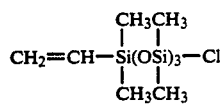

Then 1,000 mL water, 1,000 g ice, 500 mL diethyl ether, and 66.1 g (786.9 mmole) sodium bicarbonate were introduced into a stirrer-equipped four-neck flask with cooling to 0° C. A solution of 200 g (582.9 mmole) of the previously synthesized tetrasiloxane in 200 mL diethyl ether was dripped in from an addition funnel while stirring. After the completion of addition, the ether layer was separated and washed with water. Removal of the ether in vacuo at room temperature afforded 186.8 g product. This was confirmed by IR and NMR to be the tetrasiloxane with the following structural formula:

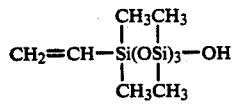

Then 186.3 g (573.8 mmole) of this tetrasiloxane, 262 g tetramethoxysilane, and 0.0354 mL propionic acid were placed in a four-neck flask equipped with stirrer and distillation set-up and were heated to 130° C. A mixture of tetramethoxysilane and methanol by-product was removed from the system by distillation, and fresh tetramethoxysilane was then added. The course of the reaction was monitored by GLC, and the process was repeated until the peak assigned to the tetrasiloxane had disappeared. A total of approximately 700 g tetramethoxysilane was used. After termination of the reaction, the fraction at 88° to 91° C./1 mmHg was collected by distillation in vacuo to yield 198.7 g product. This was confirmed by IR and NMR to be pentasiloxane with the following structural formula:

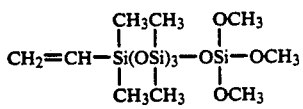

APPLICATION EXAMPLE 1

First 100 parts organopolysiloxane with average degree of polymerization of 7,000 (99.82 mole percent dimethylsiloxy units and 0.18 mole percent methylvinylsiloxy units), 40 parts wet-method silica with specific surface area of 200 m2/g, and 1.2 or 2.0 parts of the organopentasiloxane synthesized in Example 1 were blended and then mixed and kneaded in a kneader mixer. Subsequent heat treatment at 170° C. for 1.5 hours gave a silicone rubber base. Then 0.6 parts 2,5-dimethyl-2,5-di(tert-butylperoxy)hexane was mixed to homogeneity into 100 parts of this silicone rubber base to give a silicone rubber composition. This composition was press-molded for 10 minutes at 170° C./20 kg/cm2 to give a 2 mm-thick silicone rubber sheet. This silicone rubber sheet was then held for 4 hours in a forced convection over at 200° C. A dumbbell for evaluation testing was made from the resulting silicone rubber sheet, and its fatigue at a constant 100 percent stretch was measured using the De Mattia fatigue tester stipulated in Section 15 of JIS K 6301. These results are reported in Table 1.

For comparison, a silicone rubber composition was prepared as above, but in the present case using the specified quantity of silanol-terminated dimethylpolysiloxane (viscosity of 40 centistokes at 25° C.) in place of the organopentasiloxane synthesized in Examples 1. This silicone rubber composition was cured above, a dumbbell for evaluation testing was prepared from the resulting silicone rubber sheet, and its fatigue at a constant 100 percent stretch was measured using the De Mattia fatigue tester. These results are also reported in Table 1. The obtained results show that the silicone rubber moldings which employed the organopentasiloxane according to the present invention could tolerate more than 1 million elongations and exhibited a better fatigue resistance than the comparison examples.

TABLE 1

Measurement Results for Constant Elongation Fatigue Resistance

|  | Examples | | Comparison Examples | |
|---|---|---|---|---|
| organopentasiloxane, parts | 1.2 | 2.0 | 0 | 0 |
| dimethylpolysiloxane, parts | 0 | 0 | 2.0 | 0 |
| hardness (JIS A) | 48 | 49 | 47 | 53 |
| tensile strength (kgf/cm2) | 76 | 80 | 79 | 66 |
| tear strength (kgf/cm) | 10 | 7.9 | 8.0 | 6.1 |
| elongation (%) | 324 | 330 | 348 | 260 |
| cycles to failure (× 10,000) | 180 | 145 | 54 | 32 |

APPLICATION EXAMPLE 2

First 100 parts organopolysiloxane with average degree of polymerization of 7,000 (99.82 mole percent dimethylsiloxy units and 0.18 mole percent methylvinylsiloxy units), 25 parts dry-method silica with specific surface area of 300 m2/g, and 1.5 or 3.0 parts of the organopentasiloxane synthesized in Example 2

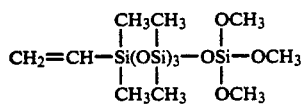

were blended and then mixed and kneaded in a kneader mixer. This was followed by heating at 170° C. for 1 hour to give a silicone rubber base. Then 0.7 parts 2,5-dimethyl-2,5-di(tert-butylperoxy)hexane was mixed to homogeneity into 100 parts of this silicone rubber base to give a silicone rubber composition. This silicone rubber composition was press-molded for 10 minutes at 170° C./20 kg/cm2 to afford a 2 mm-thick silicone rubber sheet. This silicone rubber sheet was then held for 4 hours in a forced convection oven at 200° C. A dumbbell for evaluation testing was prepared from the resulting silicone rubber sheet, and its fatigue at a constant 100 percent stretch was measured using the De Mattia fatigue tester used in Application Example 1. These results are reported in Table 2.

For comparison, a silicone rubber composition was prepared as above, but in the present case adding the prescribed quantity of vinyltrimethoxysilane or silanol-terminated dimethylpolysiloxane (viscosity of 40 centistokes at 25° C.) in place of the organopentasiloxane synthesized in Example 2. The silicone rubber composition thus obtained was cured as above, a dumbbell rubber sheet, and the fatigue at constant 100 percent elongation was measured again using the De Mattis fatigue tester. These results are also reported in Table 2.

The obtained results show that the silicone rubber moldings which employed organopentasiloxane according to the present invention could withstand over 4,000,000 elongations and had a better fatigue resistance than the comparison examples.

TABLE 2

| Measurement Results for Constant Elongation Fatigue Resistance | | | | | | |
|---|---|---|---|---|---|---|
| | Examples | | Comparison Examples | | | |
| organopentasiloxane, parts | 1.5 | 3.0 | 0 | 0 | 0 | 0 |
| vinyltrimethoxysilane, | 0 | 0 | 1.5 | 3.0 | 0 | 0 |
| parts | | | | | | |
| dimethylpolysiloxane, parts | 0 | 0 | 0 | 0 | 3.0 | 0 |
| hardness (JIS A) | 46 | 47 | 50 | 51 | 45 | 51 |
| tensile strength (kgf/cm2) | 77 | 82 | 74 | 70 | 80 | 63 |
| tear strength (kgf/cm) | 14.5 | 11.6 | 10.3 | 8.5 | 13 | 9.6 |
| elongation (%) | 318 | 347 | 282 | 251 | 385 | 255 |
| cycles to failure (× 10,000) | 422 | 383 | 193 | 185 | 97 | 80 |

That which is claimed is:

1. Organopolysiloxane with the formula

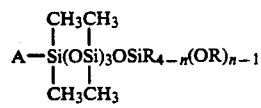

wherein A is the hydrogen atom or an aliphatically unsaturated monovalent hydrocarbon group selected from the group consisting of the norborneyl group and alkenyl group, R is selected from the group consisting of methyl, ethyl, propyl, butyl, pentyl, hexyl, vinyl, allyl, betenyl, hexenyl, isopropenyl, phenyl, tolyl, xylyl, benzyl, phenethyl, chloroethyl, nd 3,3,3-trifuloropropyl, wherein the groups R may be identical or may differ, and n is an integer with a value of 2 through 4.

2. The organopentasiloxane of claim 1 of the formula

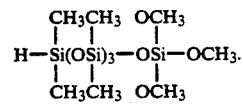

3. The organopentasiloxane of claim 1 of the formula

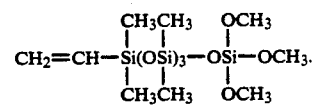

* * * * *